United States Patent [19]  [11] 4,246,898
Travalent et al.  [45] Jan. 27, 1981

[54] SYRINGE

[75] Inventors: Louis J. Travalent, Lee's Summit, Mo.; Herbert Arenson, Shawnee, Kans.

[73] Assignee: Cutter Laboratories, Inc., Berkeley, Calif.

[21] Appl. No.: 59,861

[22] Filed: Jul. 23, 1979

[51] Int. Cl.³ ............................................. A61M 5/00
[52] U.S. Cl. ................................ 128/218 P; 128/234
[58] Field of Search ......... 128/218 P, 218 PA, 218 R, 128/215 C, 216, 234, 219, 220; 222/386; 92/202, 203

[56] References Cited
U.S. PATENT DOCUMENTS

| 383,940 | 6/1888 | Brinkerhoff | 128/219 |
| 546,603 | 9/1895 | Tagliabue | 128/234 |
| 2,592,381 | 4/1952 | Blackman | 128/218 P |
| 3,016,896 | 1/1962 | Van Sickle | 128/218 P |
| 3,669,111 | 6/1972 | Dubner | 128/218 P |

Primary Examiner—John D. Yasko
Attorney, Agent, or Firm—Robert E. Allen

[57] ABSTRACT

A syringe for dispensing medicaments includes a barrel with a discharge end and an open end for receiving a plunger. The plunger has a head with engagement means for receiving a plunger seal. The plunger seal is a tubular member which is severed along a generally longitudinal direction providing a slit which allows the seal to be expanded for fitting onto the plunger head. Preferably the slit has an irregularity at the forward end which provides a locking configuration which prevents the seal from being twisted away from its normally tubular shape. For metered dose application, the shank of the plunger may be threaded for the desired placement of a stop ring threaded on the shank. In one form, the ring and barrel have interlocking means to prevent the ring from moving backward when pressure is applied to the plunger after the ring has reached the barrel.

7 Claims, 8 Drawing Figures

SYRINGE

BACKGROUND OF THE INVENTION

1. Field

This invention relates to syringes and in particular to plastic syringes, especially those intended for dispensing viscous medicament compositions.

2. Prior Art

There are problems associated with the manufacture of prefilled syringes in which satisfactory solutions have not been found. Normally, the discharge end of the syringe is first capped, the medicament is placed in the barrel to an appropriate height and the plunger is then introduced until the plunger tip with its seal comes into contact with the medicament. The air in the barrel above the medicament must be expelled in some manner during this final step. This can be accomplished either by providing an air vent in the plunger tip seal or by manually inserting a wire or similar device between the barrel wall and the seal to generate an air vent while inserting the plunger, then withdrawing the wire. The former method is unsatisfactory since the medicament can escape through the air vent. The latter method is time consuming and would not lend itself to automated prefilling techniques. The latter method also would require that the seal on the plunger tip have a thin, flexible wiper configuration but such a seal is readily subject to deformation particularly when made of plastic, which would result in an unsatisfactory seal. Seals made of rubber often are undesireable since the medicament or its vehicle may react in an unfavorable manner.

There have been a number of syringes which have been designed for metered dosage of a medicament such as those typified in U.S. Pat. Nos. 2,764,981, 2,856,925, 2,869,541, 2,875,761 and 3,934,586, all of which show various stop means on the plunger for permitting metered doses to be administered. U.S. Pat. Nos. 3,563,240 and 4,153,056 represent syringes in which fine adjustment of metered dosages are achieved by the use of a ring threadedly attached to the shaft of the plunger.

SUMMARY OF THE INVENTION

The syringe of the present invention provides a solution to the aforementioned problems and is particularly adapted for automated pre-filling of plastic disposable syringes, especially those which contain viscous medicament compositions such as pastes or the like.

The syringe of this invention comprises a barrel with a discharge end and an open end opposite for receiving a plunger. The plunger has a shaft, one end of which has finger-engaging means, and the other end or plunger head has engagement means for receiving a disengageable plunger seal. The plunger seal is a tubular member whose outer surface provides sealing contact with the interior walls of the barrel and whose inner surface has fitment means for coacting with the engagement means on the plunger head for retaining the plunger seal to the plunger. A slit extends longitudinally on the plunger seal which allows the plunger seal to be spread or expanded so that it can be fitted onto the plunger head during assembly but thereafter to assume its normally unexpanded condition. When the plunger seal is fitted into the mouth of the barrel, it becomes compressed but a very fine channel remains on the surface at the position of the slit so that air can escape from the barrel as the plunger is forced inwardly until the plunger seal contacts the medicament.

In one of the preferred embodiments of the syringe, there is one or more small longitudinal channels in the inner wall of the barrel extending from the mouth to a point somewhat above the level of the medicament stored in the barrel. This channel (or channels) facilitates the placement of the plunger to its proper depth, particularly in an automated assembly.

A preferred embodiment of the plunger seal member is one in which the slit is offset from the generally longitudinal direction for a short distance at the forward end so that the seal member is thereby supplied with an additional locking means to keep the seal from twisting open once it is engaged with the plunger head, while inserting the plunger into the barrel. In addition, the offset slit portion located at the forward end of the plunger seal helps to prevent the flow of medicament through the fine channel created by the slit as the plunger is forced down into the barrel.

Still another preferred form of the syringe particularly when used for metered dosing of the medicament, is provided by an internally threaded ring which coacts with threaded means on the shaft of the plunger and allows the ring to be located at any desired position on the shaft. The ring then acts as a stop against the mouth of the barrel to limit the depth of travel by the plunger. With small diameter syringes, the threads on the shaft of the plunger preferably have a greater pitch than the threads on large diameter syringes in order to speed the setting of the ring to a desired point, particularly where the syringe is being used in a single dose operation. When the operator pushes in on the plunger until the ring abuts the barrel, if the plunger is released, the ring may rotate backwards to relieve the pressure as a result of the greater pitch on the threads. Thus for such syringes, it is preferred that the mouth of the barrel has a ledge containing interlocking means which coact with interlocking means on the forward surface of the ring. Such coacting interlocking means prevents this backward movement of the ring and assures the dosage which the plunger has been set for will be delivered.

DETAILED DESCRIPTION OF PREFERRED EMBODIMENTS

Figure 1:
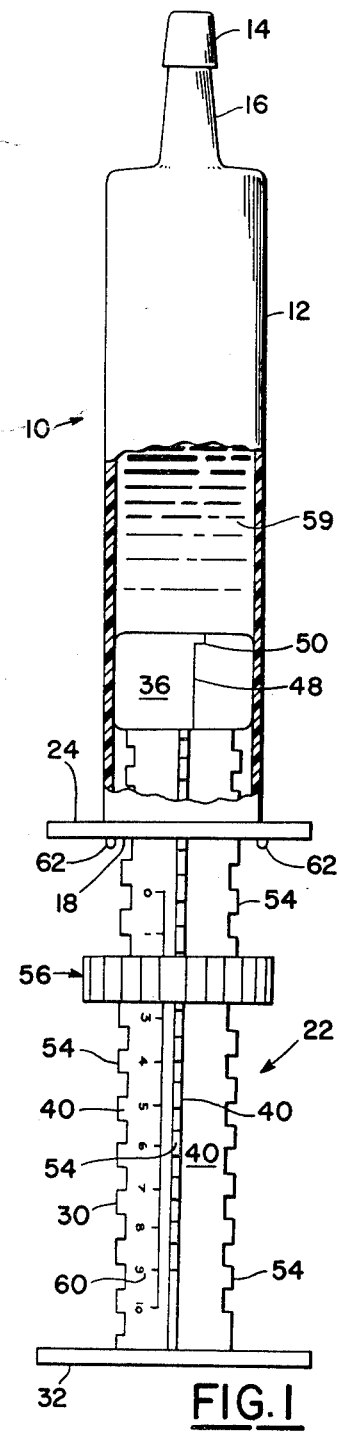
FIG. 1 is an elevational view partly in section illustrating the syringe of the present invention prefilled with a medicament.
Figure 2:
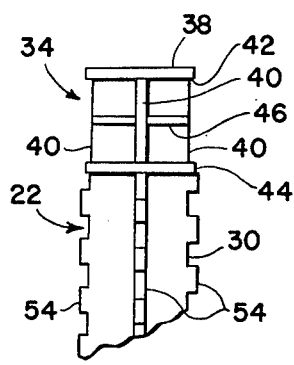
FIG. 2 is a partial elevational view of the plunger showing engagement means on the plunger head.
Figure 3:
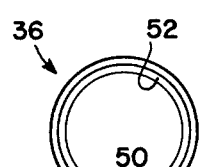
FIG. 3 is a top plan view of the plunger seal.
Figure 7:
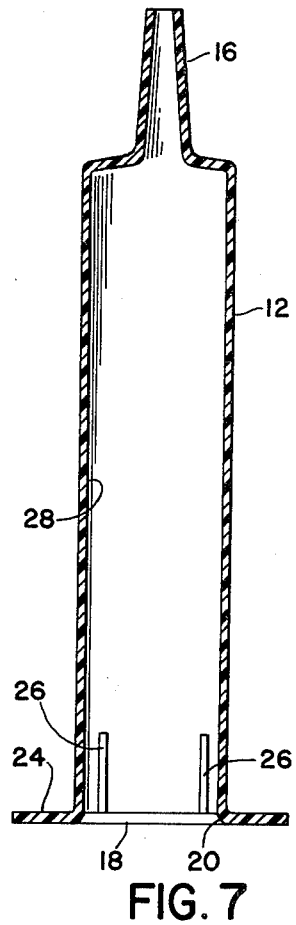
FIG. 7 is an elevational view in cross section of the barrel for the syringe.
Figure 8:
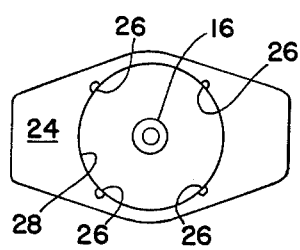
FIG. 8 is a top plan view of the barrel of FIG. 7.
Figure 6:
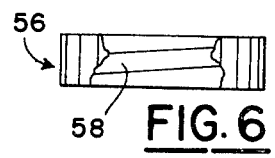
FIG. 6 is an elevational view partly in section of the length adjusting member of FIG. 5.

The syringe 10 of the present invention is represented in FIG. 1. A barrel 12 with a cap 14 on the discharge end 16 has an open end or mouth 18 which may have a slight taper 20 (FIG. 7) to facilitate the introduction of a plunger 22. Barrel 12 may also have a ledge 24 at its mouth 18. In a preferred embodiment the entrance to the barrel has four channels 26 extending from the mouth 18 for a short distance into the interior wall 28 of the barrel (FIGS. 7 and 8) which also facilitate the introduction of the plunger, particularly in automated assembly.

The plunger 22 in this embodiment comprises a shaft 30 with a ledge 32 for engagement of one's fingers at one end and a plunger head 34 at the forward end. The plunger head 34, which is adapted for coacting with and retaining a plunger seal member 36, has a circular head plate 38 extending beyond four equally spaced radial fins 40 to form a ledge 42 and a rear plate 44 having the same diameter as that of head plate 38. The plunger head 34 may also have an intermediate supporting plate 46 of smaller diameter.

Figure 4:
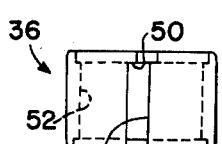
FIG. 4 is an elevational view of the plunger seal in a partly expanded condition.

Plunger seal member 36 is a tubular member having a diameter slightly larger than the diameter of the bore of the barrel 12. Seal 36 is severed in a longitudinal direction to provide a slit 48 to allow the seal to be expanded (as shown in FIG. 4) for fitting onto plunger head 34. Slit 48 may have other configurations such as a diagonal slit or any other type as long as it permits the seal member to be expanded. Preferably slit 48 has an offset or some such irregularity such as that shown at 50 to generate a locking tab or structure which help to prevent twisting of the seal away from its normal tubular configuration. Such locking means is located at the front end on the slit pathway. Seal member 36 has an intermediate portion 52 which is thicker than the walls at either end and it is this portion which fits into the recess formed between plates 38 and 44 on plunger head 34 and engages seal 36 to head 34.

To provide for metered or multiple dosage administration, shaft 30 has four radial fins 40 spaced at right angles to each other for the full length of the shaft. A multiplicity of teeth 54 are spaced on the outer edges and are staggered in relation to the teeth on one rib to those on an adjacent rib so as to provide a threaded arrangement having a certain pitch. A plunger length adjusting member or ring 56 has an internal thread 58 which is adapted to conform to the recesses between teeth 54 so that ring 56 may be rotated forward or backward on shaft 30. Ring 56 is first installed onto shaft 30 before plunger seal 36 is fitted onto plunger head 34.

Having filled barrel 12 to an appropriate level with a desired medicament compostion 59, such as an anthelmintic paste, the plunger is inserted into the mouth of the barrel and as it is forced down to the level of the medicament, air in the barrel passes first through channels 26 until seal 36 goes beyond them at which point the residual air is able to flow down the channel created by the slit 48 and escape from the syringe. Ring 56 is then rotated to a designated point on the shaft as indicated by indicia 60 and after removing cap 14, the desired dose of medicament will be delivered by pushing the plunger until ring 56 stops against ledge 24 of the barrel.

Figure 5:
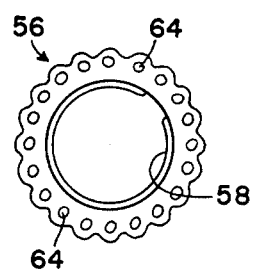
FIG. 5 is a view of the forward end of one embodiment of a plunger length adjusting member.

Syringes which have rather small diameter barrels and therefore have rather narrow shafts on the plungers, necessarily would have either smaller teeth 54 to achieve the same pitch as on longer plungers or else the pitch would be much greater if the same sized teeth were used. The smaller, single dose syringes are frequently used to place anthelmintic pastes into a horse's mouth and a veterinarian does not want to take the time to rotate a ring on the plunger if it requires a great many turns to position the ring at the proper setting. Consequently, a threaded shaft having a steeper pitch is much preferred. Unfortunately, when the plunger is forced against the paste in such a syringe, if pressure isn't maintained against the plunger, the pressure dissipates by pushing against the ring and sometimes causes it to rotate backwards. One can then not be assured the proper dose has been administered. To circumvent this problem locking means are provided on shelf 24 of the barrel and ring 56. In the embodiment shown in FIGS. 1 and 5, these means take the form of two bosses or pegs 62 projecting, one on either side of the mouth 18, on ledge 24 and a series of small cavities 64 arranged circumferentially on the forward surface of ring 56. When pegs 62 are fitted into two cavities 64, the ring is locked into place and will not move backwards under pressure.

Numerous variations within the spirit of this invention are possible and therefore it is intended that the specific examples described above should be construed as illustrative only and the scope of the invention is limited only by the claims which follow.

We claim:

1. A syringe having a barrel with a discharge end and an open opposite end for receiving a plunger, the plunger having a shaft with finger engaging means at one end and engagement means at the other end for attachment of a disengageable plunger seal, the plunger seal comprising a generally tubular member having a forward end and a rearward end and which has an outer surface adapted for sliding contact with the interior of the barrel and fitment means on its interior for coacting with the engagement means, the tubular member being severed in a generally longitudinal direction so as to provide a single slit and permitting the member to be expanded for coacting with the engagement means but thereafter assuming its normal unexpanded condition when fully coacted with the engagement means.

2. The syringe of claim 1 wherein the slit in the plunger seal has locking means at the forward end formed by an irregularity in the slit in a direction opposed to the generally longitudinal direction of the slit.

3. The syringe of claim 2 wherein the shaft has a rotatable plunger length adjusting member threadedly attached to the shaft and adapted for movement in either direction on the shaft by coacting with threaded means on the shaft, the rotatable member having a diameter sufficiently large to cause it to arrest the plunger at a preselected location within the barrel.

4. The syringe of claim 3 wherein the barrel has at least one groove on its interior surface extending longitudinally from the open end to a position part way down the barrel for a length which is approximately the length of the plunger seal.

5. The syringe of claim 4 wherein there are four grooves substantially equally spaced.

6. The syringe of claim 3 wherein the barrel has a ledge at its open end and with locking means integral with the ledge, and the rotatable member comprises an internally threaded ring with locking means on its forward surface, whereby the respective locking means of the rotatable member and the ledge of the barrel are adapted to interlock and prevent movement of the rotatable member when pressure is being exerted on the plunger.

7. The syringe of claim 6 wherein the locking means of the ledge comprise two bosses and the locking means of the rotatable member comprises a plurality of cavities arranged circumferentailly in the forward surface of the ring and adapted to receive the bosses.

* * * * *